United States Patent [19]

Watanabe et al.

[11] Patent Number: 5,608,088
[45] Date of Patent: Mar. 4, 1997

[54] PROCESS FOR PRODUCING 3,4-CARANEDIOL

[75] Inventors: Keisuke Watanabe, Ashiya; Noboru Yamamoto, Mishimagun; Atsushi Kaetsu, Toyonaka; Yoshimi Yamada, Toyonogun, all of Japan

[73] Assignee: Sumitomo Chemical Company, Limited, Osaka, Japan

[21] Appl. No.: 525,187

[22] Filed: Sep. 8, 1995

[30] Foreign Application Priority Data

Sep. 12, 1994 [JP] Japan .................................. 6-217662
Sep. 21, 1994 [JP] Japan .................................. 6-226951
Oct. 12, 1994 [JP] Japan .................................. 6-245991

[51] Int. Cl.⁶ .................................................. C07D 301/19
[52] U.S. Cl. ...................... 549/529; 549/512; 549/513; 549/523; 549/525; 549/531; 549/545; 549/546; 568/807; 568/817; 568/822; 568/823
[58] Field of Search ............................. 549/512, 513, 549/523, 525, 529, 531, 545, 546; 568/807, 817, 822, 823

[56] References Cited

U.S. PATENT DOCUMENTS

| | | | |
|---|---|---|---|
| 3,014,047 | 12/1961 | Bain et al. | 549/546 |
| 3,560,571 | 2/1971 | Kropp | 549/545 |
| 3,862,961 | 1/1975 | Sheng et al. | 549/529 |
| 3,931,249 | 1/1976 | Stautzenberger | 549/529 |
| 4,136,119 | 1/1979 | Hunter et al. | 549/545 |
| 4,485,074 | 11/1984 | Poenisch | 423/55 |
| 4,593,012 | 6/1986 | Usui et al. | 502/167 |
| 4,755,595 | 7/1988 | Gelotte et al. | 540/57 |
| 5,130,136 | 7/1992 | Shono et al. | 424/405 |

FOREIGN PATENT DOCUMENTS

| | | |
|---|---|---|
| 0476885 | 3/1992 | European Pat. Off. . |
| 60-191020 | 9/1985 | Japan . |
| 02160624 | 6/1990 | Japan . |

OTHER PUBLICATIONS

Andrew S. Kende et al., Tetrahedron Letters, A New Paradigm for Alkene. . ., vol. 35, No. 44, Oct. 31, 1994, pp. 8123–8126.

E. KH. Kazakova et al., Chemical Abstracts, Alkali–catalyzed hydration. . ., vol. 100, No. 11, Mar. 12, 1984 CA No. 85936r.

Erkki Kolehmainen, J. Chem. Soc. Persin Trans. 2, Oxygen–containing Bicyclic. . ., No. 4, 1993 Letchworth GB, pp. 641–648.

Synthetic Communication, 19, 1939–43 (1989) Payne, et al., "Reactions of Hydrogen. . .", *J. Org. Chem.*, vol. 26, 1961, pp. 659–663.

Eto, et al., "Epoxides", *Chem. Abst.*, 86, 55595d, Jul. 1976.

*Primary Examiner*—Robert E. Sellers
*Assistant Examiner*—Randy Gulakowski
*Attorney, Agent, or Firm*—Birch, Stewart, Kolasch & Birch, LLP

[57] ABSTRACT

A process for producing 3,4-caranediol of the formula [I] includes subjecting 3,4-epoxycarane, which is obtained by epoxidizing 3-carene under specific conditions, to a hydration reaction in the presence of a base catalyst in aqueous ethanol under pressure to obtain 3,4-caranediol.

11 Claims, No Drawings

PROCESS FOR PRODUCING 3,4-CARANEDIOL

FIELD OF THE INVENTION

The present invention relates to a method for producing 3,4-caranediols.

DESCRIPTION OF THE RELATED ART 3,4-Caranediol of the following formula [I] is known as an active ingredient of insecticides (JP-A Hei 5-4901/1993). However, the known processes for producing 3,4-caranediol from 3-carene by way of 3,4-epoxycarane were not always satisfactory in that the productivity of the epoxidation reaction and hydration reaction was low for obtaining the compound of the formula [I], because a large amount of solid peroxide such as m-chloroperoxybenzoic acid was required to be handled in a heterogeneous reaction system, which is not preferable to control the epoxidation reaction. Also in the hydration reaction of the epoxide, an excess amount of potassium hydroxide was employed under severe reaction conditions causing a concern over the corrosion of the reactor. Hence an advantageous process that can provide said 3,4-caranediol of the desired stereochemistry readily with good productivity has been desired.

Therefore, an object of the present invention is to provide a process that can produce 3,4-caranediol of the formula [I] with good productivity by using mild and homogeneous epoxidation and/or hydration reactions.

SUMMARY OF THE INVENTION

That is, the present invention provides a process for producing 3,4-caranediol of the formula [I]:

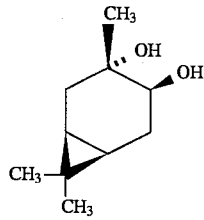

which comprises subjecting 3,4-epoxycarane of the formula [II]:

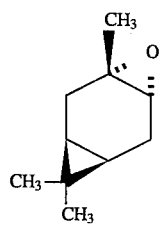

to hydration reaction in the presence of a base catalyst in aqueous ethanol under pressure. Note that in formulas [I] and [II], the bold and dashed wedges indicate the relative steric arrangements of chemical bonds.

The present invention also provides a process for producing 3,4-caranediol of the formula [I] as defined above, which comprises the steps of;

(a) reacting 3-carene of the formula [III]:

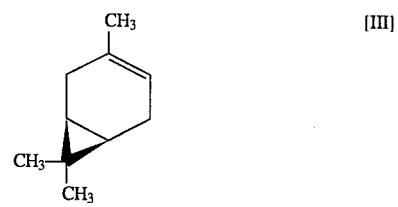

with peracetic acid in weakly basic aqueous alcohol to obtain 3,4-epoxycarane of the formula [II] as defined above; and (b) subjecting 3,4-epoxycarane obtained above to a hydration reaction in the presence of a base catalyst in aqueous ethanol under pressure to obtain 3,4-caranediol of the formula [I].

The present invention further provides a process for producing 3,4-caranediol of the formula [I] as defined above which comprises the steps of:

(a) reacting 3-carene of the formula [III] as defined above with hydrogen peroxide in the presence of a nitrile compound to obtain 3,4-epoxycarane of the formula [II] as defined above, and (b) subjecting 3,4-epoxycarane obtained above to a hydration reaction in the presence of a base catalyst in aqueous ethanol under pressure to obtain 3,4-caranediol of the formula [I].

The present invention still further provides a process for producing 3,4-caranediol of the formula [I] as defined above which comprises the steps of:

(a) reacting 3-carene of the formula [III] as defined above with an alkyl peroxide in the presence of molybdenum salt soluble in hydrocarbon to obtain 3,4-epoxycarane of the formula [II] as defined above, and (b) subjecting 3,4-epoxycarane obtained above to a hydration reaction in the presence of a base catalyst in aqueous ethanol under pressure to obtain 3,4-caranediol of the formula [I].

DESCRIPTION OF THE PREFERRED EMBODIMENT

According to the present invention, 3,4-caranediol [I] is obtained from 3,4-epoxycarane, which is obtained by epoxidizing 3-carene stereoselectively to 3,4-epoxycarane of the formula [II] with good productivity by using mild and homogeneous reactions.

In the present invention, the bold and dashed wedges shown in raw material compounds, that is, 3-carene represented by the formula [III], 3,4-epoxycarane represented by the formula [II] as an intermediate product and 3,4-caranediol represented by the formula [I] as an object compound, indicate the relative steric arrangement of chemical bonds with regards to cis/trans orientations, and 3-carene represented by the formula [III], 3,4-epoxycarane represented by the formula [II] and 3,4-caranediol of the formula [I] may be optically active substances or racemic compounds respectively.

First, description will be made of the process for producing 3,4-caranediol of the formula [I] as defined above, which comprises subjecting 3,4-epoxycarane to a hydration reaction in the presence of a base catalyst in aqueous ethanol under pressure to obtain 3,4-caranediol of the formula [I].

The reaction is usually performed at a temperature of 100° to 200° C., preferably 120° to 180° C.

The reaction pressure is usually 5 to 15 kg/cm$^2$(G).

The base catalyst to be used includes, for example, an alkali metal hydroxide such as lithium hydroxide, sodium hydroxide and potassium hydroxide, and alkali metal carbonate such as, for example, sodium hydrogen carbonate, potassium hydrogen carbonate, sodium carbonate, potassium carbonate and the like. Preferred is sodium hydroxide.

The amount of the base to be used is not limited and may be a catalytic amount, and may be, for example, less than 1 mole to 1 mole of the 3,4-epoxycarane. The weight ratio of the base to the total weight of the aqueous ethanol and the base is usually 1 to 10%, preferably 2 to 5%, particularly for industrial production.

The aqueous ethanol solvent usually contains 10 to 50% of ethanol in the total volume of the solvent, and 1 to 3 volumes, preferably 3 or more volumes of water per 1 volume of 3,4-epoxycarane [II] is used in this process.

3,4-Caranediol of the formula [I] can be separated from the reaction solution after completion of the reaction by a conventional after-treatment such as washing, concentrating and the like, and/or rectification, if necessary.

Next, description will be made of the process for producing 3,4-caranediol of the formula [I] as defined above, which comprises the steps of;

(a) reacting 3-carene of the formula [III] as defined above with peracetic acid in weakly basic aqueous alcohol to obtain 3,4-epoxycarane of the formula [II] as defined above, and (b) subjecting 3,4-epoxycarane to hydration reaction in the presence of a base catalyst in aqueous ethanol under pressure to obtain 3,4-carenediol of the formula [I].

The peracetic acid to be used in the process (a) is usually employed in a form of acetic acid solution or aqueous acetic acid solution and the concentration of peracetic acid is usually 25 to 60%, and preferably is 35 to 50%. Peracetic acid obtained in situ by reacting acetic acid or acetic anhydride with hydrogen peroxide can be used.

Molar ratios of peracetic acid to 3-carene [III] are usually 1:1 to 2:1, preferably 1:1 to 1.2:1.

The epoxidation reaction is conducted in weakly basic aqueous alcohol in the present process. The aqueous alcohol is prepared by mixing alcohol such as methanol, ethanol, propanol, isopropanol and the like with water in a ratio of 50:50 to 90:10 in volume ratio.

The reaction is usually conducted by dropping peracetic acid to the weakly basic aqueous alcohol solution of 3-carene [III]. The pH of the weakly basic aqueous alcohol solution is preferably kept at from 8 to 9.

In order to keep the solution weakly basic, 0.2 to 2.0 moles, preferably 0.8 to 1.2 moles of a base such as sodium hydrogen carbonate, potassium hydrogen carbonate, sodium carbonate, potassium carbonate, disodium hydrogen phosphate, dipotassium hydrogen phosphate and the like per 1 mole of peracetic acid is usually added to the aqueous alcohol.

Alternatively, control of the pH of the solution may be carried out by dropping separately and simultaneously peracetic acid and the base solution such as aqueous sodium hydroxide solution and the like.

The reaction temperature is usually 0° C. to room temperature, preferably 0° to 10° C.

3,4-Epoxycarane [II] thus produced can be separated by a usual after-treatment such as washing, concentrating and the like after decomposing excessive peracetic acid in the reaction solution after completion of the reaction by contacting with an aqueous sodium hydroxide solution or a solution of $Na_2SO_3$, NaOCl, $Na_2S_2O_3$ and the like, if necessary. Then the solution is subjected to the hydration reaction under specified reaction conditions as described above.

Next, description will be made on the process for producing 3,4-caranediol of the formula [I] as defined above, which comprises the steps of:

(a) reacting 3-carene of the formula [III] as defined above with hydrogen peroxide in the presence of a nitrile compound to obtain 3,4-epoxycarane of the formula [II] as defined above, and (b) subjecting 3,4-epoxycarane to a hydration reaction in the presence of a base catalyst in aqueous ethanol under pressure to obtain 3,4-carenediol of the formula [I].

The process (a) is illustrated in detail as follows.

The reaction temperature is usually from room temperature to 80° C., preferably 55° to 65° C.

The nitrile compound to be used includes an alkyl nitrile such as acetonitrile, propionitrile or isobutyronitrile, or an aromatic nitrile such as benzonitrile and the like As hydrogen peroxide, 25 to 75%, preferably 35 to 60% aqueous hydrogen peroxide is usually used.

The amount of hydrogen peroxide and the nitrile compound is usually 1.0 to 5.0 moles, preferably 1.5 to 2.5 moles, respectively per 1 mole of 3-carene of the formula [III].

The reaction is preferably performed by dropping hydrogen peroxide to the solution of 3-carene of the formula [III] and the nitrile compound so as to keep the pH of the solution at 7.5 to 8.0.

The pH of the solution is kept at 7.5 to 8.0, for example, by dropping hydrogen peroxide and an aqueous alkali such as sodium hydroxide aqueous solution and the like at the same time to the solution, but $Na_2HPO_4$ and the like may be added as a pH buffer, if necessary.

3,4-Epoxycarane [II] can be separated by a conventional after-treatment as described above.

Next, description will be made of the process for producing 3,4-caranediol of the formula [I] as defined above which comprises the steps of:

(a) reacting 3-carene of the formula [III] as defined above with an alkyl peroxide in the presence of molybdenum salt soluble in hydrocarbon to obtain 3,4-epoxycarane of the formula [II] as defined above, and (b) subjecting 3,4-epoxycarane to a hydration reaction in the presence of a base catalyst in aqueous ethanol under pressure to obtain 3,4-carenediol of the formula [I].

The alkyl hydroperoxide includes, for example, tert-butylhydroperoxide, ethylbenzenehydroperoxide and the like. The content of the alkyl hydroperoxides is usually adjusted by dilution with an organic solvents to a range of 25 to 60%, preferably 30 to 40%.

The molybdenum salt soluble in hydrocarbon can be obtained, for example, by heating ammonium molybdate and the hydrocarbon carboxylic acid having 4 to 30 carbons (e.g., naphthenic acid and the like) in the presence of the organic amine (e.g.,tributylamine and the like) usually 150° to 250° C., preferably 170° to 220° C.

1.0 To 5.0 moles of the hydrocarbon carboxylic acid having 4 to 30 carbons and 0.1 to 1.0 mole of the organic amine are usually used per 1 mole of the ammonium molybdate. The amount of molybdenum salt soluble in hydrocarbon to be used is usually 0.01 to 1.0% of the alkyl hydroperoxide.

The reaction is usually performed in an organic solvent(i.e., hydrocarbon solvent). The organic solvents to be used include, for example, saturated hydrocarbon solvents such as hexane, heptane, 2,2,4-trimethylpentane and the like, aromatic hydrocarbon solvents such as benzene, toluene, xylene, ethylbenzene and the like, halogenated hydrocarbon solvents such as methylene chloride, chloroform, 1,2-dichloroethane, chlorobenzene and the like. The most preferred is toluene.

In this epoxidation reaction, water content of 3% or less is preferable and excessive water content may adversely affect the reaction, so the solvent to be used is usually dried over magnesium sulfate, ammonium sulfate, sodium sulfate or the like before use.

The reaction temperature is preferably from 50° C. to the boiling point of the solvent or 100° C.

The amount of the alkyl hydroperoxide is usually 1.0 to 3.0 mole, preferably 1.5 to 2.5 mole per 1 mole of 3-carene of the formula [III].

3,4-Epoxycarane of the formula [II] thus produced is separated and further subjected to the hydration reaction as described above.

EXAMPLES

The present invention is illustrated in detail by the following Examples but not restricted by these Examples. In the following Examples wt % is refered to merely as % unless otherwise noted.

Example 1

40.8 grams of (+)-3-carene, 180 ml of ethanol, 90 ml of water and 30g of sodium carbonate were charged in 500 ml 5-necked flask under nitrogen gas atmosphere and stirred. 65 G of acetic acid solution (containing about 10% of water) of 38.4% peracetic acid was dropped for 6 hours, while keeping the reaction temperature at 0° C. and pH at 8.5 to 9.0 by dropping 40% sodium hydroxide aqueous solution separately and simultaneously with peracetic acid, and then reacted for 18 hours at room temperature. Successively, unreacted peracetic acid was decomposed by adding 40% aqueous sodium hydroxide solution.

Next, after ethanol was removed by distillation under reduced pressure, 50 g of saturated brine was added and an oil layer washed twice was settled and separated 36 grams of the oil layer (crude 3,4-epoxycarane of the formula II) obtained by the separation was charged with 30 g of ethanol and 70 g of 5% sodium hydroxide aqueous solution in 1 liter autoclave equipment (SUS-316) and reacted for 20 hours at 170° C. (11 kg/cm$^2$). After the reaction mixture was settled and an oil layer was separated. After it was washed with 50 ml of saturated brine and distilled water in order, it was concentrated to give 37 g of crude product.

1S, 3S, 4S, 6R-Carane-3,4-diol (retention time: 31 min./areal percentage: 80%) and its isomer; 1S, 3R, 4R, 6R-carane-3,4-diol (retention time: 30 min./areal percentage: 8%) as a by-product were detected by gas chromatography.

The crude reaction product was rectified to give 31 g of a mixture of 1S, 3S, 4S, 6R-carane-3,4-diol and 1S, 3R, 4R, 6R-carane-3,4-diol distilled at 145° C./(10 to 12 mmHg) with a content ratio of 10:1, the total content was 96%, the net yield from (+)-3-carene was 60%.
Condition of Gas chromatography Measurement
Column: Widebore GC capillary column HR-20M (30 m in length :0.53 mm in diameter);
Column temperature: Enhanced from 100° to 160° C. at 5° C./min. and then kept at the final constant temperature;
Injection and detection temperature: 240° C.

In the following Examples, the gaschromatography analysis was conducted under the same conditions described above.

Referential Comparative Example 1

36 grams of the crude 3,4-epoxycarane obtained by the method described in Example 1 was charged with 30 g of methanol and 70 g of 5% sodium hydroxide in the 1 liter autoclave equipment (SUS-316) and reacted for 20 hours at 130° C. (4 kg/cm$^2$). After the reaction mixture was settled, the oil layer was separated. After it was washed with 50 ml of saturated brine and distilled water in that order, it was concentrated to give 37 g of the crude product.

1S, 3S, 4S, 6R-Carane-3,4-diol (retention time: 31 min./areal percentage: 40%), its isomer, 1S, 3R, 4R, 6R-carane-3,4-diol (retention time: 30 min./areal percentage: 4%) as a by-product and its alkylether (1S, 3S, 4S, 6R-3-methoxy-4-hydroxycarane: retention time: 10.5 min./areal percentage: 32 %) seldom obtained as a by-product in Example 1 were detected by the gas chromatography analysis.

The crude reaction product was rectified to give about 13.5 g of the alkylether, 1S, 3S, 4S, 6R-3-methoxy-4-hydroxycarane distilled at 105° C./(10 to 12 mmHg) with the purity of 90%, and 16 g of the mixture of 1S, 3S, 4S, 6R-carane-3,4-diol and 1S, 3R, 4R, 6R-carane-3,4-diol with the content ratio of 10:1 distilled at 145° C./(10 to 12 mmHg), the total content was 96% and the net yield from (+)-3-carene was 31%.

Thus, the yield resulting from the use of methanol in place of ethanol as in the process of Example 1, was inferior.

Referential Comparative Example 2

36 grams of the crude 3,4-epoxycarane obtained by the method described in Example 1 was charged with 30 g of isopropanol and 70 g of 5% sodium hydroxide aqueous solution in a 1 liter autoclave equipment (SUS-316) and reacted for 20 hours at 160° C. (8 kg/cm2). After the reaction mixture was settled, an oil layer was separated. After it was washed with 50 ml of saturated brine and distilled water in order, it was concentrated to give 34 g of a crude product.

1S, 3S, 4S, 6R-carane-3,4-diol (retention time: 31 min./areal percentage: 36%) and its isomer, 1S, 3R, 4R, 6R-carane-3,4-diol (retention time: 30 min./areal percentage: 3%) as a by-product were detected. 3,4-Epoxycarane as the raw material (retention time: 6.5 min./areal percentage: 50%) remained unreacted.

The crude reaction product was rectified to give about 13.6 g of the mixture of 1S, 3S, 4S, 6R-carane-3,4-diol and 1S, 3R, 4R, 6R-carane-3,4-diol with the content ratio of 10:1 distilled at 105° C./10 to 12 mmHg. Total content was 96%, the net yield from (+)-3-carene was 28%. Besides, 16 g of the 3-α-Epoxycarane distilled at 80° C./10 to 12 mmHg was recovered. Thus, the resulting yield from the use of isopropanol in place of ethanol as in the process b of Example 1, was inferior.

Referential Comparative Example 3

46 grams of the crude 3,4-epoxycarane obtained by the method described in Example 1 was charged with 100 g of 5% sodium hydroxide aqueous solution in the 1 liter autoclave equipment (SUS-316) and reacted for 20 hours at 170° C. (6 kg/cm2). After the reaction mixture was settled, an oil layer was separated. After it was washed with 50 ml of saturated brine and distilled water in that order, it was concentrated to give 41 g of a crude product.

1S, 3S, 4S, 6R-Carane-3,4-diol (retention time: 31 min./ areal percentage: 27%) and its isomer, 1S, 3R, 4R, 6R-carane-3,4-diol (retention time: 3 0 min./areal percentage: 3%) as a by-product were detected by gas chromatography analysis of the crude product.

Furthermore, 3,4-Epoxycarane as the raw material (retention time: 6.5 min./areal percentage: 60%) was found to be unreacted.

The crude reaction product was rectified to give 10 g of the mixture of 1S, 3S, 4S, 6R-carane-3,4-diol and 1S, 3R, 4R, 6R-carane-3,4-diol distilled at 145° C./(10 to 12 mmHg) with the content ratio of 10:1, total content was 96%, the net yield from (+)-3-carene was 19%. Besides, 22 g of 3,4-epoxycarane distilled at 80° C./(10 to 12 mmHg) was recovered. Thus, the resulting yield from the use of no ethanol as in the process b of Example 1 was inferior to the yield when ethanol was used.

Example 2

40.8 grams of (+)-3-carene, 114 g of ethanol, 5 g of water, 30.75 g of acetonitrile and 0.375 ml of an aqueous solution of 0.1M $Na_2HPO_4$ were charged in 500 ml 5-necked flask under nitrogen atmosphere and stirred. 51 grams of 50% aqueous hydrogen peroxide was dropped for 6 hours simultaneously with 5 ml of 40% sodium hydroxide solution and then reacted for 18 hours at 60° C.

Then the solution was cooled to room temperature and the unreacted hydrogen peroxide was decomposed by adding 15 g of $Na_2SO_3$, so that the temperature should not exceed 40° C.

Next, after ethanol was removed by distillation under reduced pressure, 50 g of saturated brine was added and oil layer was settled and separated, then washed twice with water.

42 grams of the oil layer (crude 3,4-epoxycarane) obtained by separation was charged with 30 g of ethanol and 70 g of 5% aqueous sodium hydroxide solution in 1 liter autoclave equipment (SUS-316) and reacted for 20 hours at 170° C. (11 kg/cm$^2$). After the reaction mixture was settled, the oil layer was separated. After it was washed with 50 ml of saturated brine and distilled water in order, it was concentrated to give 41 g of crude product.

1S, 3S, 4S, 6R-Carane-3,4-diol (retention time: 31 min./ areal percentage: 80%) and its isomer, 1S, 3R, 4R, 6R-carane-3,4-diol (retention time: 30 min./ areal percentage: 7%) as a by-product were detected by gaschromatography analysis of the crude product.

The crude reaction product was rectified to give 35 g of the mixture of 1S, 3S, 4S, 6R-carane-3,4-diol and 1S, 3R, 4R, 6R-carane-3,4-diol distilled at 145° C./(10 to 12 mmHg) with the content ratio of 10:1, total content 96%, the net yield from (+)-3-carene of 60%

Example 3

40.8 grams of (+)-3-carene, 114 g of methanol, 5 g of water, 30.75 g of acetonitrile and 0.375 ml of aqueous solution of 0.1 M $Na_2HPO_4$ were charged in 500 ml 5-necked flask under nitrogen atmosphere and stirred. 51 g of 50% aqueous hydrogen peroxide was dropped for 6 hours while keeping the reaction temperature at 60° C. and pH at 7.5 to 8.0 by dropping 5 ml of 40% sodium hydroxide solution simultaneously, and then reacted for 18 hours at 60° C.

Then, the solution was cooled to room temperature and the unreacted hydrogen peroxide was decomposed by adding 15 g of $Na_2SO_3$ such that the temperature did not exceed 40° C.

Next, after ethanol was removed by distillation under reduced pressure, 50 g of saturated brine was added and oil layer was settled and separated, then washed twice with water.

42 GRAMS of the oil layer (crude 3,4-epoxycarane) obtained by separation was charged with 30 g of ethanol and 70 g of 5% sodium hydroxide aqueous solution in 1 liter autoclave equipment (SUS-316) and reacted for 20 hours at 170° C. (11 kg/cm$^2$). After the reaction mixture was settled, the oil layer was separated. After it was washed with 50 ml of saturated brine and distilled water in order, it was concentrated to give 41 g of a crude product.

1S, 3S, 4S, 6R-carane-3,4-diol (retention time: 31 min./ areal percentage: 73%), its isomer, 1S, 3R, 4R, 6R-carane-3,4-diol (retention time:3 0 min./percentage in size: 7%) as a by-product were detected by the gas chromatography.

The crude reaction product was rectified to give 35 g of the mixture of 1S, 3S, 4S, 6R-carane-3,4-diol and 1S, 3R, 4R, 6R-carane-3,4-diol distilled at 145° C.(10 to 12 ramrig) with the content ratio of 10:1, total content was 96% and the net yield from (+)-3-carene was 69%.

Example 4

40.8 grams of (+)-3-carene and 150 mg of the molybdenum salt soluble in hydrocarbon (obtained by heating 5.5 g of ammonium molybdate, 18.5 g of naphthenic acid and 4.0 g of tributylamine for 10 hours at 200° C. in 200 ml flask while water generated was removed at the same time) were charged in 500 ml 5 necked flask under nitrogen atmosphere, and the resultant was heated to 97° C. and stirred. 43.2 g of the tert-butylhydroperoxide in toluene solution (the concentration of the tert-butylhydroperoxide was 37.5% and the content of water was 1.69%) was added to the flask for 2 hours at the same temperature and reacted for 4 hours at the same temperature.

Then, 150 g of 40% sodium hydroxide aqueous solution was added, stirred for 30 minutes, and the unreacted tert-butylhydroperoxide was decomposed as above.

Next, after 150 g of saturated brine was added and the toluene layer was washed twice by water, the solution was settled and separated.

After the toluene layer obtained by the separation was dried with anhydrous magnesium sulfate, it was concentrated to give 42.3 g of crude 3,4-epoxycarane.

42 GRAMS of the said crude 3,4-epoxycarane was charged with 30 g of ethanol and 70 g of 5% sodium hydroxide aqueous solution in 1 liter autoclave equipment (SUS-316) and reacted for 20 hours at 180° C. (11 kg/cm$^2$). After the reaction mixture was settled, the oil layer was separated. After it was washed with 50 ml of saturated brine and distilled water in order, it was concentrated to give 37 g of a crude product.

1S, 3S, 4S, 6R-Carane-3,4-diol (retention time: 31 min./ areal percentage:80%) and its isomer, 1S, 3R, 4R, 6R-carane-3,4-diol (retention time: 30 min./areal percentage: 8%) as a by-product were detected by gas chromatography analysis of the crude product.

The crude reaction product was rectified to give 35 g of the mixture of 1S, 3S, 4S, 6R-carane-3,4-diol and 1S, 3R, 4R, 6R-carane-3,4-diol distilled at 145° C./(10 to 12 mmHg) with the content ratio of 10:1, total content was 96% and the net yield from (+)-3-carene was 68%.

What is claimed is:

1. A process for producing 3,4-caranediol of the formula [I]:

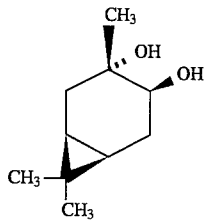

which comprises subjecting 3,4-epoxycarane of the formula [II]:

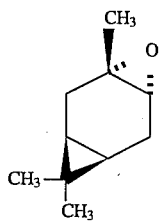

to a hydration reaction in the presence of a base catalyst in aqueous ethanol under pressure.

2. A process for producing 3,4-caranediol of the formula (I) as defined in claim 1, which comprises reacting 3-carene of the formula (III):

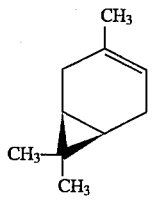

with peracetic acid in weakly basic aqueous alcohol to obtain 3,4-epoxycarane as defined in claim 1, and then subjecting 3,4-epoxycarane of the formula (II) obtained above to a hydration reaction in the presence of a base catalyst in aqueous ethanol under pressure.

3. A process for producing 3,4-caranediol of the formula (I) as defined in claim 1, which comprises reacting 3-carene of the formula (III)

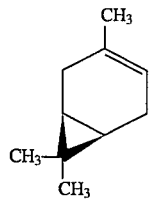

with hydrogen peroxide in the presence of a nitrile compound to obtain 3,4-epoxycarane as defined in claim 1, and then subjecting 3,4-epoxycarane of the formula (II) obtained above to a hydration reaction in the presence of a base catalyst in aqueous ethanol under pressure.

4. A process for producing 3,4-caranediol of the formula (1) as defined in claim 1, which comprises reacting 3-carene of the formula (III)

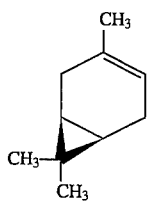

with an alkyl hydroperoxide in the presence of a molybdenum salt soluble in hydrocarbon, and then subjecting 3,4-epoxycarane of the formula (II) obtained above to a hydration reaction in the presence of a base catalyst in aqueous ethanol under pressure.

5. A process according to claim 2, wherein pH of the weakly basic aqueous alcohol is kept at 8 to 9.

6. A process according to claim 3, wherein the nitrile compound is acetonitrile.

7. A process according to claim 3, wherein the epoxidation reaction is conducted at pH 7.5 to 8.0.

8. A process according to claim 4, wherein the molybdenum salt soluble in hydrocarbon is obtained by heating ammonium molybdate and C4 to C30 hydrocarboncarboxylic acid in the presence of an organic amine.

9. A process according to claim 4, wherein the molybdenum salt soluble in hydrocarbon is obtained by heating ammonium molybdate and naphthenic acid in the presence of tributylamine.

10. A process according to claim 4, wherein the alkyl hydroperoxide is tert-butylhydroperoxide.

11. A process according to any one of claims 1 to 10, wherein the base catalyst is sodium hydroxide.

* * * * *